United States Patent
Gundersen et al.

(12)

(10) Patent No.: US 6,273,165 B1
(45) Date of Patent: Aug. 14, 2001

(54) PROCESS LINE FOR THE MANUFACTURE OF ABSORBENT DISPOSABLE ARTICLES

(75) Inventors: Dag H Gundersen, Tolvsrød; Harald Børresen, Stokke; Odd F. Johansen, Tønsberg, all of (NO)

(73) Assignee: Molnlycke AB, Gothenburg (SE)

( * ) Notice: Subject to any disclaimer, the term of this patent is extended or adjusted under 35 U.S.C. 154(b) by 428 days.

(21) Appl. No.: 08/750,041
(22) PCT Filed: May 23, 1995
(86) PCT No.: PCT/SE95/00584
  § 371 Date: Nov. 29, 1996
  § 102(e) Date: Nov. 29, 1996
(87) PCT Pub. No.: WO95/32696
  PCT Pub. Date: Dec. 7, 1995

(30) Foreign Application Priority Data

May 31, 1994 (SE) .................................................. 9401869

(51) Int. Cl.[7] ............................. B35B 35/00; A61F 13/15
(52) U.S. Cl. ......................... 156/367; 156/538; 156/543; 156/552; 156/598; 604/358
(58) Field of Search ..................................... 156/556, 538, 156/350, 367, 368, 543, 552, 598; 604/358

(56) References Cited

U.S. PATENT DOCUMENTS 5,383,988 * 1/1995 Hermann et al. .
5,492,591 * 2/1996 Hermann et al. .

FOREIGN PATENT DOCUMENTS 0 589 859   3/1994 (EP) .

* cited by examiner

*Primary Examiner*—Curtis Mayes
(74) *Attorney, Agent, or Firm*—Young & Thompson

(57) ABSTRACT

A production line for manufacturing absorbent disposable articles includes a conveyor path (3, 14, 15) which moves a web of material through the production line, and a row of devices (1, 4, 5, 6, 7, 8, 9, 11, 12, 13) which are arranged sequentially in the movement direction of the conveyor path and which perform different operations in the manufacture of the absorbent article. The devices are carried by rectangular carrier plates (29, 34, 35, 39, 47) which are attached to vertical posts (17) which, in a framework (16), are placed on the same side of the conveyor path and sequentially in a direction parallel with the movement direction of the conveyor path. The framework includes a plurality of connectors (27, 28) which connect to flowing media delivery lines, such as electric current and compressed air.

12 Claims, 4 Drawing Sheets

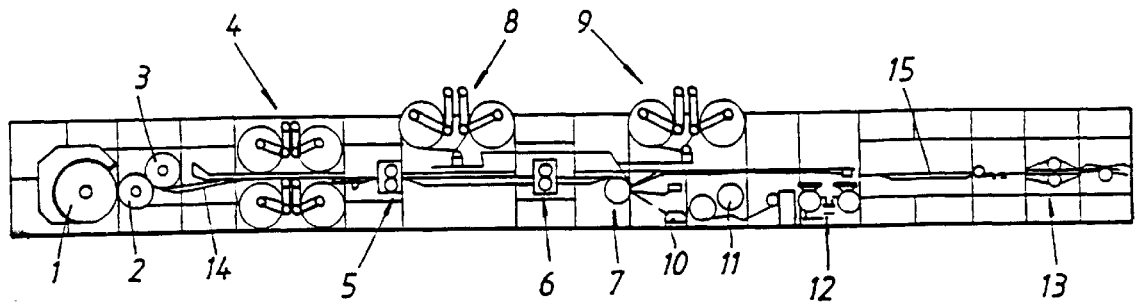
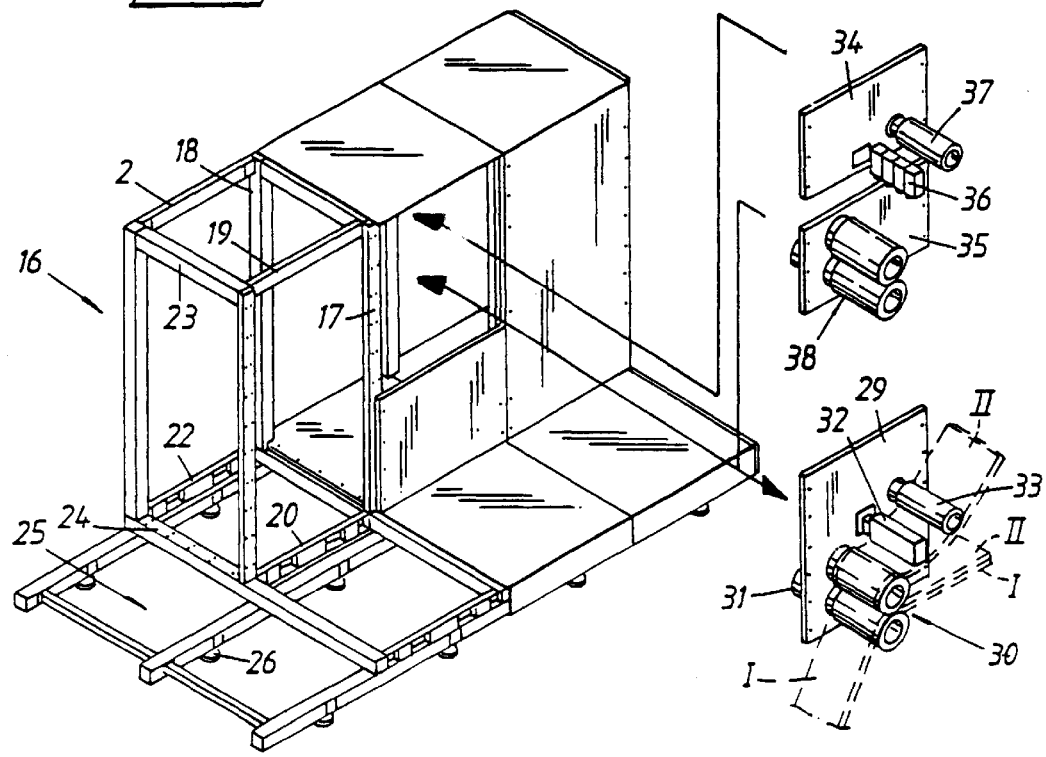

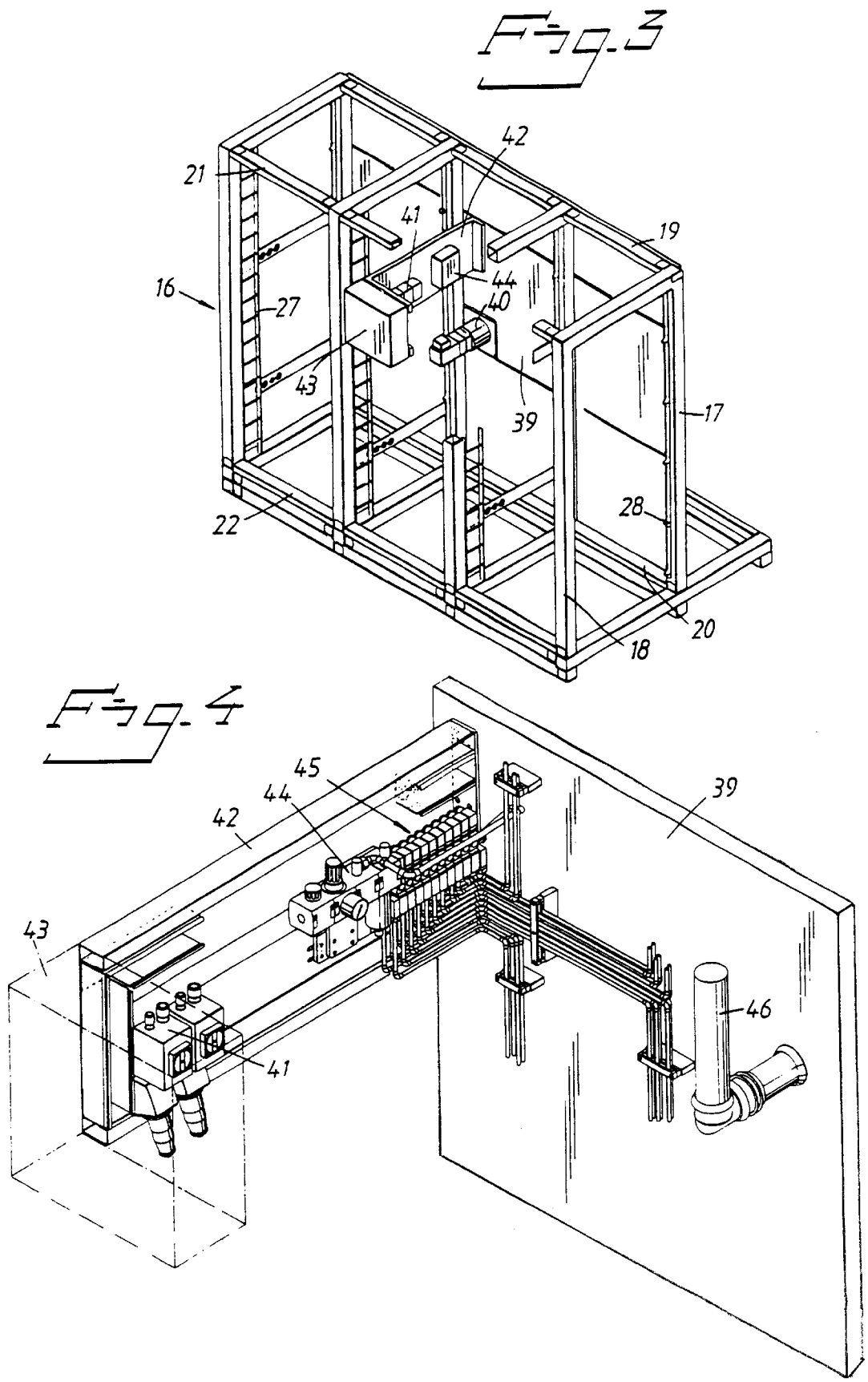

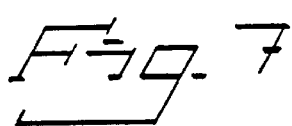
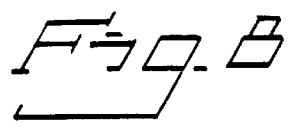
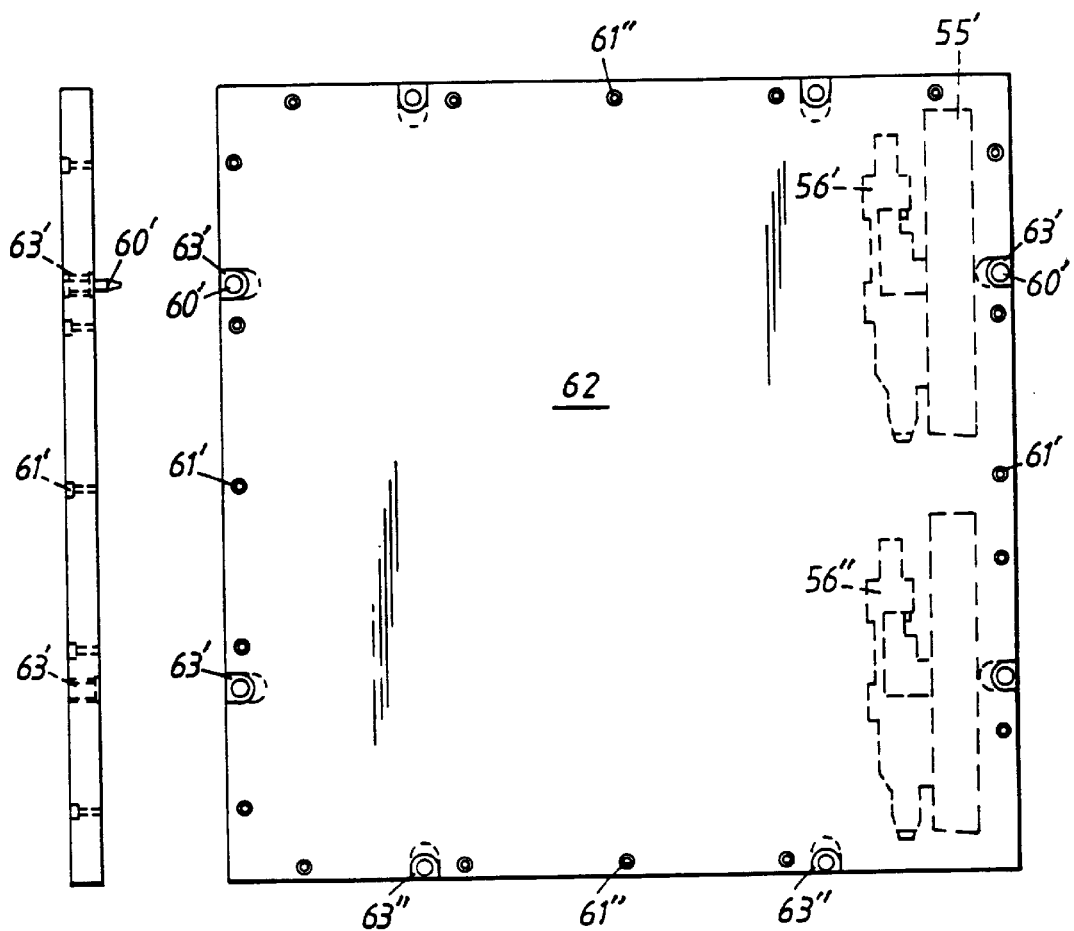

PROCESS LINE FOR THE MANUFACTURE OF ABSORBENT DISPOSABLE ARTICLES

The present invention relates to a production line for the manufacture of absorbent disposable articles, such as diapers, sanitary napkins and incontinence guards, wherein the production line includes a conveyor path which functions to move a web of material through the production line, and a row of devices are arranged sequentially in the direction of web movement for carrying out different working operations included in the manufacture of the absorbent article, these devices being carried on rectangular carrier plates which are attached to vertical posts which are placed in a framework on mutually the same side of the conveyor path and sequentially in a direction which extends parallel with the direction of conveyor-path movement.

Absorbent disposable articles are typically produced by taking a web of material from a storage reel and moving the web past a number of devices which perform different operations in sequence, such as placing absorbent bodies on the web, laying-out elastic, applying glue, applying further webs of material, compressing absorbent bodies, and heat-welding or ultrasonic-welding the webs, and so on. In production of this nature, the production line has been traditionally constructed as one single unit. In recent times, production development has accelerated within this particular technical field, necessitating comprehensive reconstruction of the production lines. However, production lines of unit construction are less suitable for reconstruction and as a result, it has taken much too long to introduce new or modified products onto the market, and it has often been necessary to refrain from making small improvements to existing products, because of the radical changes in the production lines that such an improvement would incur, while, at the same time, the long non-productive times or down-time caused by such reconstruction would prevent the market demand of such products being met, resulting in loss in profits and, in the longer term, perhaps also a loss in the share of the market.

The European Patent Application No. 93850174.9 teaches a production line for the manufacture of absorbent disposable articles which overcomes these drawbacks to a large extent. The various working devices of the production line are carried by mutually identical module plates which can be mounted in any desired position in a framework that extends along the production line. This design greatly facilitates reconstruction of the production line, while enabling the production line to be extended by adding further working devices thereto, without needing to make large modifications.

The primary object of the present invention is to further facilitate restructuring of a production line and the addition of further working devices, in comparison with the aforesaid known production line. A secondary object of the invention is to facilitate mounting of the carrier plates in a production line, so that a large part of this work can be carried out by technically unqualified personnel.

These objects are achieved in accordance with the invention with a production line of the kind defined in the introduction which is characterized in that the framework includes a plurality of mutually adjacent connections which are connected to delivery lines for flowing media, such as electric current and compressed air; in that each carrier plate supporting at least one working device, which is operated or maneuvered by flowing media, also supports operating or maneuvering means and connecting elements for connecting the operating or maneuvering means concerned to a corresponding connector on the framework; and in that the connectors on the framework and the connector elements are so arranged that each connector element on a carrier plate can be connected to a connector on the framework irrespective of the position of the carrier plate on the framework. This construction greatly simplifies fitting of a carrier plate in the production line, since all that is needed is to secure the plate to the framework and to connect the connector elements to the nearest line fixed connector on the framework. This fitting operation can be carried out very quickly and with the aid of technically unqualified personnel. The down-time of such a production line will be relatively short when changing or fitting a working device.

In one preferred embodiment of the invention, the framework includes at least one row of sets of connectors for electric current and compressed air arranged sequentially in the direction of the conveyor path, wherein these sets of connectors are separated by a distance which is equal to a multiple of the smallest distance between the vertical posts. Each set of connectors on the framework includes a databus connector, and each carrier plate supports a working device which includes a control means which is connectable to the databus connector, and a connector-element holder which is placed in the same position on each carrier plate.

The invention will now be described with reference to the accompanying drawings, in which FIG. 1 is a schematic front view of one embodiment of an inventive production line;

FIG. 2 is a schematic, perspective view taken obliquely from the front of part of the framework and the carrier plates included in the production line illustrated in FIG. 1;

FIG. 3 is a perspective view taken obliquely from the rear of the framework illustrated in FIG. 2;

FIG. 4 is a perspective rear view of a carrier plate provided with a connector element holder;

FIGS. 7 and 8 are respectively a schematic side view and a schematic top view taken from the front of one embodiment of an inventive carrier plate.

Figure 5:
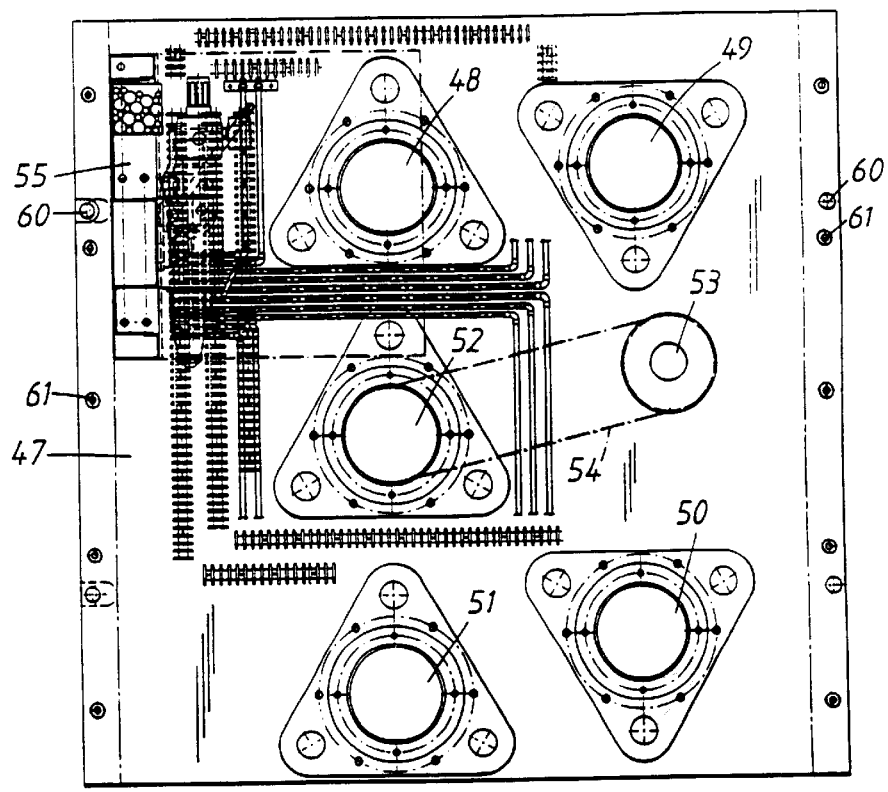
FIGS. 5 and 6 are respective top views taken from the rear and from the side of a carrier plate which supports a number of alternating current motors and compressed-air lines.

FIG. 1 illustrates very schematically a diaper production line which, as seen in the direction of manufacture, i.e. from left to right in the Figure, includes a mat-laying wheel 1, a compression wheel 2, a transfer wheel 3, a device 4 for feeding layers from a top and a bottom reel-stand, a pair of compression rolls 5, a transverse cutter 6, a transfer device 7, feeders 8, 9, a thread applicator 10, an adhesive tape applicator 11, feeder means 12, and a cutter 13. The production line also includes means for conveying the diaper blank through the line, for instance the conveyors 14, 15 illustrated schematically in the Figure.

When manufacturing a diaper in the aforedescribed production line, the mat-laying wheel 1 produces a layer of cellulose fluff which is transferred to the conveyor 14 with the aid of the compression wheel 2 and the transfer wheel 3. The fiber mat then passes through the device 4, in which a top and a bottom layer of tissue taken from storage reels are delivered to the top and the bottom of the cellulose fluff mat or layer respectively. These layers then pass together through the roll pair 5 and are compressed therebetween. This results in a coherent, continuous three-layer body which passes through the transverse cutter 6, which produces individual absorbent bodies from the continuous, coherent three-layer body. A transfer wheel 7, also called an accelerator wheel, places the absorbent body on a web of plastic film, for instance polyethylene film, which is taken from a storage reel in the forward feed means 12 and advanced to the wheel 7 from right to left in the Figure, and thereafter from left to right in said Figure with the individual absorbent bodies spaced a given distance apart. Prior to arriving at the wheel 7, the plastic film passes the adhesive tape applicator 11, which provides the plastic film with a pair of fastener tapes, and will also have passed the thread applicator 10 which provides the plastic film with appropriate elastic. The forward feed devices 8, 9 function to lay two layers of nonwoven fabric, taken from reel stands included in said devices, on top of the plastic film web and the absorbent bodies, and the top and bottom layers are fastened together in some suitable way, for instance by gluing or ultrasonic welding. Finally, the web of absorbent bodies enclosed between top layers, i.e. the two nonwoven layers, and bottom sheet, i.e. the plastic film, pass through a cutter 13 by means of which complete diapers are cut from the web.

The choice of appropriate known working devices capable of performing the aforesaid functions lies in the normal competence of the person skilled in this field, and the design of the working devices 1–13 and the conveyors 14, 15 included in the production line will naturally depend on the type of diaper to be manufactured. The design, or construction, of the individual working devices forms no part of the present invention and the application will not therefore be laden with a detailed description of the components included in the production line.

In accordance with the present invention, the aforesaid working devices are mounted in the production line on carrier plates which, in turn, are mounted on a framework 16.

FIGS. 2 and 3 are respectively schematic, perspective front and rear views of parts of the framework 16 included in the production line. The side of the framework facing the conveyors and the viewer of FIGS. 1 and 2 is the front side of the framework. The framework 16 is constructed from two parallel rows of front and rear vertical posts 17 and 18 respectively, which are evenly spaced in the rows. The mutually sequential posts 17 and 18 in said rows are connected together by top and bottom cross-bars 19, 20 and 21, 22 respectively, and mutually opposing posts in the working direction of the production line are joined together by additional top and bottom cross-bars 23, 24. Naturally, further cross-bars may be included if necessary for mechanical strength reasons, although this is avoided if possible, at least in the front row of posts 17, so as not to restrict the possibility of positioning working devices on carrier plates attached to the framework. The bottom cross-bars 24 extend beyond the front posts 17. The framework rests on a carrier frame 25 which includes height-adjustable legs 26.

As illustrated schematically in FIG. 3, cable ladders 27 are arranged on the rear vertical posts 18. These cable ladders include heavy-current conductors and weak-current conductors through which current is supplied to the working devices of the production line, and a network cable is also connected to a central computer. Arranged within the front vertical posts 17 are compressed-air lines, and a row of compressed-air outlets 28 is placed along the length of said posts.

As before mentioned, the working devices are carried by carrier plates, which are screwed firmly to the front vertical post 17 of the framework 16. The size of these carrier plates is adapted to a large extent to the size of the working device which the plate concerned is intended to carry or support, as indicated in FIGS. 1 and 2, which makes the production line highly flexible. FIG. 2 illustrates an example of how this flexibility can be utilized. The Figure shows a carrier plate 29 which carries a roll pair 30 driven by an alternating current motor 31. The plate 29 also carries a gluing unit 32 provided with a slot-shaped nozzle (not shown) and a guide roller 33. Also shown in FIG. 2, in broken lines, is a first web of material I which is glued to a second web of material II in the nip of the roll pair 30, this web II having passed beneath the glue nozzle of the glue applicator 32 prior to entering the roll nip. If it is later decided that the webs I and II can be joined together equally as well with glue beads, the carrier plate 29 can be removed quickly and easily from the framework 16 and replaced with another carrier plate that carries a different type of glue applicator. In the FIG. 2 illustration, the carrier plate 29 has been replaced with two carrier plates 34 and 35, which carry a glue applicator 36 which includes a row of glue nozzles, and a guide roller 37 and a driven roll pair 38 respectively. The carrier plates 34, 35 have the same width as the carrier plate 29, but are only half as high.

FIGS. 3 and 4 are schematic, perspective rear views of a carrier plate 39 which carries a working device, for instance a driven roll pair, whose drive motor 40 is mounted on the rear side of the carrier plate 39. The drive motor 40 is comprised of an alternating current motor whose output shaft passes through the carrier plate and coacts with the working device (not shown) mounted on the front: of the plate. The drive motor is connected, by conductors not shown, to safety switches 41 mounted on a holder 42. The safety switches can, in turn, be connected to the nearest cable ladder 27 on the framework 16, with the aid of appropriate connectors, for instance plug-in connectors. The holders 42 are always arranged in the same position on a carrier plate that carries a working device, more specifically in the upper right-hand corner of the illustrated inventive carrier plate, as seen from the front. As a result, there is only a short distance between holder and the nearest cable ladder, meaning that a short conductor can be used from the holder 42, one end of this conductor being connected to the male part of the plug-in contact. In order to make this length of the conductor short, several female connector parts are spaced in the height direction along the cable ladders.

The holder 42 also carries a control unit 43 by means of which the working device is controlled, this unit, in turn, being connected to a central computer which controls all working devices included in the production line, via the network cable or conductor in the cable ladders. The holder 42 also carries a compressed-air unit 44, which is connected to the nearest compressed-air outlet 28, by means of a suitable hose coupling. As shown schematically in FIG. 4, the unit 44 includes a row of compressed-air valves 45, from which air-lines lead to pneumatic piston-cylinder devices (not shown) included in the working devices mounted on the front side of the carrier plate. Pneumatics are normally used to move the working devices into and out of their respective working positions, for instance to move the rolls of a roll pair towards and away from one another, although other applications, such as pneumatic motors, can be used within the scope of the invention. FIG. 4 also shows a pipe 46 which can be connected by means of a suitable hose coupling to a sub-pressure source, for instance a vacuum box, which is often positioned beneath a conveyor in the production line provided with a row of coupling outlets. Naturally, it is also possible to provide a pipe system which is connected to a sub-pressure source in or outside the vertical posts 17 or 18 in a manner similar to the compressed air supply arrangement, or to provide a row of coupling outlets along the posts. As will be understood, hydraulic fluid connections may also be arranged in the rows of connector arrays when hydraulic motors are used in the production line.

Figure 6:
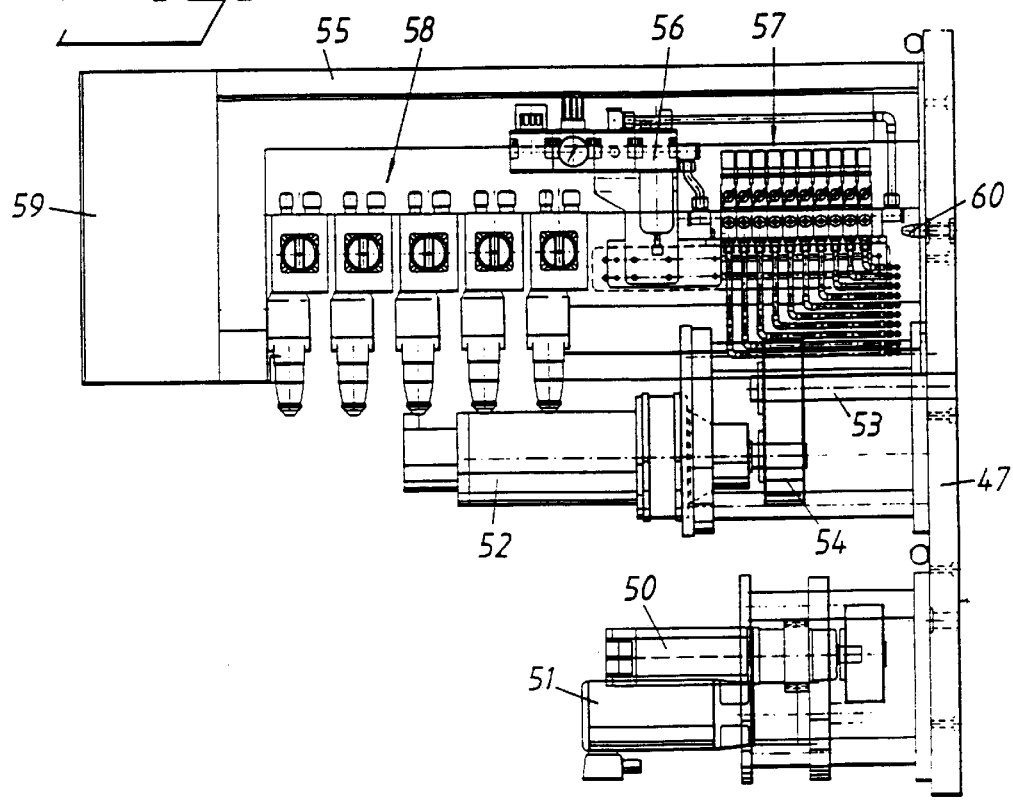

FIGS. 5 and 6 illustrate another carrier plate 47 on which five alternating current motors 48, 49, 50, 51 and 52 are mounted, of which only the motors 50–52 are shown in FIG. 6. The motor 52 drives a shaft or axle 53, via a belt 54 shown in chain lines in FIG. 5. The working devices mounted on the front side (not shown) of the carrier plate may comprise a cutter which is operated by two drive motors, and a combined transporting and compressing unit which uses three motors. Similar to the case of the carrier plate 39 shown in FIGS. 3 and 4, a connector-element holder 55 is attached to the carrier plate 47 and placed in its upper right-hand corner as seen from the front side of the carrier plate. The holder supports a compressed-air unit 56 and a set of compressed-air valves 57 and a set 58 of safety switches for the motors 48–52. The holder 55 also carries a control unit 59, which is connected to the network cable via a data bus connection. The carrier plate 47 is provided along both of its edges with a row of holes 61 through which the bolts used to screw the plate to the framework are inserted. In order to enable the carrier plate 47 to be fitted more easily, so that these holes will lie in register with corresponding screw-threaded holes in the framework posts, the carrier plate is also provided with guide pins 60 which are intended to coact with appropriate guide surfaces on the framework posts, for instance upwardly extending V-shaped surfaces, so as to ensure that the plate will be brought quickly to its correct position.

The control units 43, 59 include all components necessary to regulate individual operation of the working devices carried by the carrier plate or carrier plates 39, 47, and can therefore be operated from outside the production line, therewith enabling the function of a repaired working device to be tested without needing to first replace the repaired working device in the production line. The primary purpose of the central computer is to synchronize operation of the different working devices in the production line and to monitor working of the production line so as to stop work as soon as one of the working devices is found to malfunction.

FIGS. 7 and 8 illustrate schematically a further embodiment of an inventive carrier plate 62. This carrier plate differs from the carrier plate 47 shown in FIGS. 5 and 6 essentially by virtue of including two holders 55', 55" arranged one after the other along the right edge-part of the carrier plate 62, and also by virtue of including a row of fastener holes 61', 61" along all edges of the plate. The working device mounted on the carrier plate 62 has not been shown in these Figures for the sake of clarity. Components that correspond to similar components in FIGS. 5 and 6 have been identified by the same reference signs to which a prime and double-prime have been added in FIGS. 7 and 8. Because the plate 62 includes a row of fastener holes 61', 61" along each edge, the carrier plate can be mounted with the two opposing rows 61' or the two opposing rows 61" coacting with rows of holes (not shown) in the posts, therewith further increasing the flexibility of the production line. With the intention of facilitating fitting of a carrier plate, the guide pins 60', and also the guide pins 60 shown in FIGS. 5 and 6, are mounted on the plate 62 in a manner which enables the pins to be readily fitted and removed, by screwing the pins into and out of sockets or sleeves 63', 63" in the plate 62.

As the size of the carrier plates is determined essentially by the size of the working device or devices that the plates are intended to carry, the space for accommodating each working device in the production line is also determined in practice by the size of the device. However, the dimensions of the carrier plates must be proportionate to one another in a particular manner, so as to enable the plates to be exchanged and to achieve the desired flexibility of the production line. Thus, the sizes of the carrier plates must be such as to enable each carrier plate to be replaced with or exchanged for one or more other carrier plates. To this end, the lengths of the sides of the carrier plates are essentially a multiple of the length of the smallest side of the smallest carrier plate, and the carrier plates are so dimensioned that each carrier plate will include a pair of opposing sides whose lengths are generally equal to or comprise generally a multiple of the distance between the posts 17. The fact that the lengths are not exact multiples of the length of the smallest side of the smallest carrier plate is due to the fact the carrier plates shall be spaced some small distance apart on the framework, so as to make fitting and dismantling of the plates easier. For practical reasons, this distance should be at least 2 mm and the length of the smallest side of the smallest plate should be at least 400 mm.

The working devices of the inventive illustrated production line are mounted by placing the carrier plates supporting the working devices included in the production line in place in the framework and screwing the plates securely thereto. The quick-couplings of the holders 42, 55 intended for the delivery of flowing media, i.e. electric current, compressed air, etc., are then coupled to the delivery linen provided in the framework, and the control devices 43, 59 controlling the working devices are connected to the central computer by means of databus connections. The production line is ready to be put into operation when all working devices have been secured and connected-up. Fine adjustment, or trimming, of the fitted working devices is unnecessary, since these devices are constructed as independent units which possess their own drive means and control units, the different operations of which are controlled and synchronized by a central computer. It thus suffices to check that the individual working devices function in the manner intended. To replace or add a working device in the production line, is thus a measure that can be performed quickly therewith making the downtime for such a measure short. Furthermore, adaptation of the size of the carrier plates to the size of associated working devices enables available space on the framework to be utilized more effectively, so that additional working devices can be added to the production line without requiring comprehensive restructuring. Because each carrier plate that supports a working device forms an independent unit which can be operated independently, comprehensive restructuring of the production line can also be effected in a very short period of time; in theory, the minimum restructuring time is the time taken to remove one carrier plate and fit another.

The vertical posts 17 included in the framework 16 are preferably secured to the remainder of the framework in a manner which enables the posts to be easily dismantled. This enables posts that are located behind carrier plates of such size as to extend between three sequential posts 17 in the Figures to be dismantled so as not to be in the way of working devices mounted on such a plate. When the plate does not extend along the full height of the framework, a cross-bar is suitably fitted between the posts so as to give further support to the plate. To this end, the vertical posts are conveniently provided with a row of cross-bar attachments extending along the length of said posts.

As indicated in FIGS. 1 and 2, the outer surfaces of the framework 16 are completely clad with carrier plates, even at those places where no working devices are carried. Although not shown in the drawings, strips are arranged in the spaces between mutually adjacent carrier plates. These strips may have the form of sealing strips provided with resilient sealing lips and will be of a nature that enables them to be fitted and removed easily. The interior of the framework is thus a closed space. This prevents dust and dirt from reaching the operating and control components that are enclosed in this space and, at the same time, enables an appropriate type of cooling unit (not shown in the drawings) to be placed in the centre of the space for central cooling of said components. It is pointed out that the rear and side walls of the framework need not be comprised of carrier plates according to the aforegoing, but may be comprised of conventional wall elements to no disadvantage, wherein a door which provides access to the interior of the framework may be provided in one of these walls.

As shown in FIGS. 2 and 3, the bottom cross-bars 24, which extend forwardly beyond the front posts 17 transversely thereto are also covered with carrier plates. According to one variant of the invention, the conveyors are mounted on these plates by means of quick-couplings, to facilitate fitting of the carrier plates secured to the posts 17.

In the described embodiment, the production line is comprised of carrier plates of different sizes. It will be understood, however, that the invention can also be applied in production lines comprised of carrier plates that have mutually the same size.

It will be understood that the described and illustrated exemplifying embodiment of an inventive production line can be modified in many ways within the scope of the invention. For instance, the framework may include props or braces between the posts 18, for supporting heavy working devices that project far out from the plate and therewith prevent such devices from bending. Correspondingly, props or braces can be attached to the carrier frame 25 on the front side, so as to prevent bending of long rolls. It is also possible to provide the framework with glue delivery connections. Furthermore, the sets of connections may be fitted to solely each alternate rear post 18. In this case, it may be convenient to place the connector holders of two mutually adjacent, laterally positioned carrier plates on laterally opposite sides of the carrier plates. Thus, the invention includes all constructions in which the distance between connector sets in said rows of connectors form a multiple of the smallest distance between the vertical posts and those constructions in which the holders are placed on several standardized locations along the edge parts of the plates. The roof of the framework may also be used to support particularly bulky working devices, such as reel racks, for instance. Sealing strips may also be placed along the opposing front edges of the posts, within the region of the fitted carrier plates, wherein only those horizontal spaces between the plates need be covered by sealing strips. The invention is therefore limited solely by the content of the following Claims.

What is claimed is:

1. A production line for manufacturing absorbent disposable articles, wherein the production line includes a conveyor path (3, 14, 15) which moves a web of material through the production line, and a row of devices (1, 4, 5, 6, 7, 8, 9, 11, 12, 13) which receive operating energy from a flowing media and which are arranged sequentially in the movement direction of the conveyor path and which perform different working operations in the manufacture of the absorbent article, wherein said devices are carried by rectangular carrier plates (29, 34, 35, 39, 47) which are attached to vertical posts (17) which are placed in a frame-work (16) on the same side of the conveyor path and sequentially in a direction parallel with the movement direction of the conveyor path;

a plurality of connectors (27, 28) which connect to lines for the delivery of the flowing media, one of said connectors being provided for each pair of said vertical posts carrying at least one of said carrier plates;

in that each of said carrier plates (29, 34, 35, 39, 47) carries associated operating means (31, 40, 48–52) for operating one or more of the devices carried by the respective one of said carrier plates and connector elements (41, 44, 45, 56, 57, 58) for connecting the operating means to a corresponding one of said connectors (27, 28) on the framework, wherein said connector elements carried by the respective said carrier plate are connected to said connectors in the one of said pair of vertical posts carrying the respective said carrier plate; and in that said connectors and said connector elements are so arranged that each said connector element can be connected to one of said connectors on the framework irrespective of the position in which the carrier plate is placed on the framework.

2. A production line according to claim 1, wherein the framework (16) includes at least one row of sets of connectors (27, 28) for electric current and compressed air, wherein said connector sets are disposed sequentially in the movement direction of the conveyor path and are mutually spaced by a distance which constitutes a multiple of the distance between the vertical posts (17).

3. A production line according to claim 2, wherein each set of connectors on the framework includes a databus connection; and in that each said carrier plate (39, 47) carrying a working one of the devices includes a control unit (43, 59) connectable to the databus connection.

4. A production line according to claim 1, wherein each said carrier plate (39, 47) which carries a working one of the devices includes a holder (42, 55) for said connector elements (41, 43, 44, 45, 56, 57, 58) which are placed in an identical position on each of said carrier plates.

5. A production line according to claim 4, wherein at least one of the carrier plates (62) carrying at least one of the working devices includes plural connector-element holders (55', 55") placed sequentially along one side-edge part of the carrier plate.

6. A production line according to claim 1, wherein each said carrier plate (62) whose sides all have a length which is generally equal to or exceeds the smallest distance between the posts (17) can be fastened to the framework in at least one first position and in at least one second position which corresponds to rotation of the plate (62) through 90° in its plane relative to the first position.

7. A production line according to claim 1, wherein a plurality of said connectors comprise a row of cable ladders (27) which each extend vertically adjacent one of the vertical posts (17) in the framework, wherein the cable ladders include male and female devices which can be connected to female or male devices connected to a holder (42, 55) on a one of the carrier plates supporting a working one of the devices.

8. A production line according to claim 7, wherein the cable ladders (27) include a plurality of vertically spaced male or female devices.

9. A production line according to claim 7, wherein the cable ladders (27) extend vertically opposite each vertical post (17) in the framework (16) with the exception of one of the two outermost ones of the vertical posts.

10. A production line according to claim 1, wherein said connectors comprise at least one compressed-air outlet (28).

11. A production line for the manufacture of absorbent disposable articles, comprising:

plural carrier plates, each for carrying at least one device used in the manufacture of the absorbent disposable articles, each device being powered by flowing media;

a framework comprising vertical posts, each of said carrier plates being carried by at least two of said vertical posts so that the devices carried by said carrier plates are sequentially arranged for the manufacture of the absorbent disposable articles;

a connector carried in one of each set of the two vertical posts carrying one of said carrier plates, each of said connectors being connected to a source of the flowing media; and each of said carrier plates further comprising a receptor for conveying the flowing media to the device on the corresponding one of the carrier plates and for being connected to the one said connector on the one of the vertical posts carrying the corresponding one of the carrier plates.

12. The production line of claim 11, wherein a distance from said receptor to said corresponding connector is less than a distance between two adjacent said vertical posts.

* * * * *

UNITED STATES PATENT AND TRADEMARK OFFICE
CERTIFICATE OF CORRECTION

PATENT NO.     : 6,273,165 B1
DATED          : August 14, 2001
INVENTOR(S)    : Gundersen et al.

It is certified that error appears in the above-identified patent and that said Letters Patent is hereby corrected as shown below:

<u>Title page,</u>
Item [*], delete "428" and insert -- 0 --.

Signed and Sealed this

First Day of July, 2003

JAMES E. ROGAN
*Director of the United States Patent and Trademark Office*